(12) United States Patent
Kim et al.

(10) Patent No.: US 9,102,647 B2
(45) Date of Patent: Aug. 11, 2015

(54) METHOD FOR PREPARING LACTIDE USING AN IONIC SOLVENT

(71) Applicant: Hyundai Motor Company, Seoul (KR)

(72) Inventors: Si Hwan Kim, Gyeonggi-do (KR); Chae Hwan Hong, Seoul (KR); Do Suck Han, Gyeonggi-do (KR); Ji Yeon Seo, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 14/061,088

(22) Filed: Oct. 23, 2013

(65) Prior Publication Data

US 2014/0187798 A1 Jul. 3, 2014

(30) Foreign Application Priority Data

Dec. 31, 2012 (KR) ........................ 10-2012-0157953

(51) Int. Cl.
*C07D 319/00* (2006.01)
*C07D 319/12* (2006.01)

(52) U.S. Cl.
CPC .................................... *C07D 319/12* (2013.01)

(58) Field of Classification Search
CPC ..................................................... C07D 319/12
USPC ........................................................ 549/274
See application file for complete search history.

(56) References Cited

U.S. PATENT DOCUMENTS 8,686,164 B2 * 4/2014 Kunnari et al. ............... 549/419

FOREIGN PATENT DOCUMENTS

| JP | 11-209370 | 8/1999 |
| JP | 2004149419 A | 5/2004 |
| KR | 10-2010-0005820 | 1/2010 |
| WO | 9205167 A1 | 4/1992 |

OTHER PUBLICATIONS

Xiaolei Wang et al. Journal of Chemical Industry and Engineering, 2007, 58(12), 3082-3085.*
Xiaolei Wang et al. Journal of Chemical Industry and Engineering, 2007, 58(12), 3082-3085, English Transaltion.*
Tsukegi et al. teach, in "Racemization behavior of L,L-lactide during heating", Polymer Degradation and Stability 92 (2007) 552-559.*

* cited by examiner

*Primary Examiner* — Nizal Chandrakumar
(74) *Attorney, Agent, or Firm* — Mintz Levin Cohn Ferris Glovsky and Popeo, P.C.; Peter F. Corless

(57) ABSTRACT

Disclosed is a method for preparing lactide by using a solvent. According to the method, since an ionic liquid is used as a solvent in a second step in the course of preparing lactide, it is possible to secure mobility of the resulting reactant, and decrease a reaction temperature. In addition, the ionic liquid absorbs moisture generated during the reaction, and thus prevents degradation of lactide which is susceptible to moisture. Furthermore, to the present method allows for the preparation of lactide successively through the continuous supply of lactic acid oligomers. Because the use of an ionic liquid minimizes the contamination of a reactive group with by-products, the use of a solvent for reactor washing is unnecessary. Further, owing to a high boiling point of the ionic liquid, the ionic liquid can be easily harvested and recycled.

6 Claims, 1 Drawing Sheet

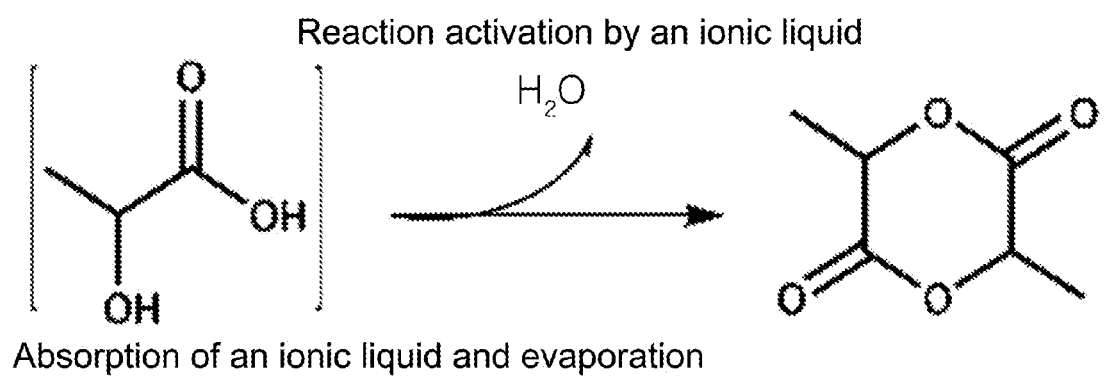

METHOD FOR PREPARING LACTIDE USING AN IONIC SOLVENT

CROSS-REFERENCE TO RELATED APPLICATION

This application claims under 35 U.S.C. §119(a) the benefit of Korean Patent Application No. 10-2012-0157953 filed on Dec. 31, 2012, the entire contents of which are incorporated herein by reference.

BACKGROUND (a) Technical Field

The present disclosure relates to a method for preparing lactide, particularly by reacting lactic acid oligomers in the presence of an ionic solvent.

(b) Background Art

The amazing industrialization since the 20th century appears to be largely based on fossil fuel resources, particularly petroleum. With the rapid industrial development and population growth, the petroleum consumption has been increased continuously as well. Petroleum is an unrenewable resource with a limited amount of reserves that will soon be exhausted. Recently, it has been found that the carbon dioxide generated by fossil fuel consumption is one of the main causes of global warming. As such, researchers are striving to improve fuel efficiency so as to reduce carbon dioxide emissions and to reduce dependence on petroleum.

Polymers derived from plants, i.e., biomass polymers, can be prepared by a chemical or biological process from renewable plant resources such as corn, bean, sugar cane, wood, etc. A value of biomass polymers lies in their potential to solve environmental problems through carbon dioxide reduction rather than in biodegradability. Among biomass polymers, polylactic acid is a carbon neutral, environment-friendly, thermoplastic, linear aliphatic polyester, It is derived from corn starch or potato starch through fermentation or it is prepared by polymerizing sugar monomers obtained from saccharification of plant-derived cellulose followed by fermentation.

Despite the various advantages of polylactic acid, however, it does not appear to be suitable for use in automobile parts, because of its low impact resistance, low heat deflection temperature, etc., as compared to the petroleum-based chemical polymers. In particular, polylactic acid has low impact strength due to its brittleness, which thus delimits its application in automobile parts.

For this reason, industrial application of polylactic acid resin is limited due to its inferior physical properties when compared to the general-use polymer materials. In particular, for use in automobile engine and chassis parts requiring high heat resistance and impact resistance, improvement of the physical properties of polylactic acid resin is essential. As a strategy to solve this problem, a technique of preparing a stereo-complex resin by blending the optical isomers of polylactic acid is often used.

Conventionally, a method for manufacturing lactide is composed of polymerizing lactic acid into a low molecular weight oligomer and depolymerizing the low molecular weight oligomer into lactide. In the first step, the oligomer is polymerized under the conditions of 150° C. and 0.3 atm, and moisture generated during this step is removed. In the second step, the synthesis of lactide is carried out in the presence of a catalyst, wherein the catalyst may include tin powder, tin halides or tin carboxylates (EP Patent Nos. 261,572 and 275,581); tin alkoxides (United Kingdom Patent No. 1,007,347); and zinc or tin (EP Patent No 264,926 and U.S. Pat. No. 4,797,468).

In this conventional method, since the polymerization and depolymerization occur simultaneously in the second step of preparing lactides, the molecular weight of lactide obtained thereby is gradually increased. Thus, in order to improve the reaction yield by inducing the synthetic reaction continuously, there is a need to increase a reaction temperature continually. In particular, the synthesis of lactide initiates under the conditions of 170° C. and 0.1 atm in the presence of LiCO as a catalyst. However, the reaction temperature should be increased gradually up to 200° C. or higher so as to increase the reaction yield. It was reported that a yield above 90% was obtained through the reaction at 200° C. for 2 hours based on a 500 cc reactor. Since the synthesis of lactide is carried out at a high reaction temperature, there is a need to wash a reactor by using a solvent, and thus, there is a problem in generating a large quantity of waste liquid caused by the solvent. Further, since the washing step is indispensable, it is very difficult to utilize continuous processing in this conventional method.

As one conventional method for preparing lactide, Korean Patent No. 171,432 describes a method for preparing lactide by treating a aqueous lactic acid feed so as to remove water therefrom, terminating the treatment to produce a crude lactide product, and separating lactides from the crude lactide product.

Japanese Patent Application Publication No. 2004-0149419 describes a method for preparing lactide, which is characterized by azeotropic dehydration of a mixture including water-containing crude lactide and an azeotropic solvent, precipitation of lactide by using the solvent after the azeotropic dehydration, solid/liquid separation of the solvent into a solid phase and an azeotropic solvent phase, and collection of lactide from the solid phase.

Japanese Patent Application Publication No. 1999-0209370 describes a method for preparing lactide, which includes the steps of: synthesizing a composition including polylactic acid alone or polylactic acid and lactide through dealcoholization by heating lactic acid ester in the presence of a monobutyltin compound, and synthesizing lactide by heating the composition polylactic acid alone or polylactic acid and lactide obtained in the above step in the presence of a monobutyltin compound.

Korean Patent Application Publication No. 2010-0005820 describes a method for preparing optically pure lactide, including: (A) dissolving lactic acid in an organic solvent; (B) adding an enzyme to the organic solvent solution of lactic acid and stirring the resulting mixture; and (C) separating optically pure lactide from the resulting mixture.

However, none of the preparation methods describes in the above patents can overcome the problems of the prior art as mentioned above.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art. In particular, the present invention provides a synthetic lactide reaction that can be carried out through continuous processing, particularly through elimination of a washing step.

In one aspect, the present invention provides a method for preparing lactide through continuous processing by reacting lactic acid oligomers in the presence of an ionic solvent. The continuous processing is preferably carried out while regulating a reaction temperature and/or pressure, particularly by regulating a reaction temperature and pressure in such a way so as to allow for elimination of a washing step.

In an exemplary embodiment, the present invention provides a method for preparing lactide, including the following steps of:

(a) adding an ionic solvent to lactic acid oligomers synthesized through the polymerization of a lactic acid monomer; and (b) synthesizing lactide from the lactic acid oligomers added to the ionic solvent while regulating a temperature and/or a pressure.

According to various embodiments, the temperature and pressure are regulated so as to allow for the synthesis of lactide without requiring a washing step.

Other aspects and exemplary embodiments of the invention are discussed infra. The above and other features of the invention are discussed infra.

EFFECT OF THE INVENTION

The technical features and advantages of the present invention are summarized as follows:

(i) Owing to the use of an ionic liquid as a solvent, it is possible to secure mobility of a reactant, to reduce a reaction temperature, to absorb moisture generated during the synthetic reaction, and thus, to prevent degradation of lactide, which is susceptible to moisture.

(ii) By reacting the oligomer in the presence of an ionic liquid, it is possible to continuously synthesize lactide through sequential addition of the oligomer, and to minimize contamination of a reactor caused by by-products. As a result, there is no need to use a solvent for washing a reactor in which the reaction is carried out.

(iii) It is easy to recover and recycle an ionic liquid formed during the reaction due to a high boiling temperature thereof. In other words, during the reaction, the temperature level is such that the ionic liquid that is formed is typically evaporated and thus recovered and recycled.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIG. 1 schematically illustrates the method for preparing lactide according to an embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about".

According to one aspect, the present invention provides a method for preparing lactide, including:

(a) adding an ionic solvent to lactic acid oligomers, wherein the lactic acid oligomers are any synthesized through the polymerization of lactic acid monomers; and (b) synthesizing lactide from the lactic acid oligomers added to the ionic solvent by regulating a temperature and/or a pressure, preferably be regulating both temperature and pressure.

According to an exemplary embodiment of the present invention, the polymerization of lactic acid monomer in the step (a) is carried out at a temperature of about 120 to 300° C. under a pressure of about 1 to 500 mmHg for about 1 to 5 hours. However, the various conditions suitable for lactide synthesis (e.g., temperature, pressure and time) can vary, and thus the conditions for polymerization can include all the conditions involved in the polymerization process where lactic acid monomers are converted into lactic acid oligomers. As such, while the above noted range is preferable, the temperature is not limited to the defined conditions.

In an exemplary embodiment of the present invention, the synthesis of lactide in the step (b) is carried out at a temperature of about 100 to 1000° C. under a pressure of about 1 to 600 mmHg for about 1 to 5 hours.

In an exemplary embodiment of the present invention, the ionic liquid is used for the purpose of ensuring stability at a high temperature condition during the step of preparing lactide. Since there is no upper limit to a boiling point of the ionic liquid, and the thermal degradation thereof easily occurs at a high temperature, it is possible to ensure stability of a solvent even at a high temperature.

In one example of the present invention, the ionic solvent suitable for the lactide synthesis includes 1-butyl-1-methyl-azepanum bis(trifluoromethylsulfonyl)imide; 1-butyl-1-methyl-azepanum dicyanamide; 6-azonia-spiro[5,6]dodecan bis(trifluoromethylsulfonyl)imide; 6-azonia-spiro[5,6]dodecan dicyanamide; 1-benzyl-3-methylimidazolium chloride 1-butyl-1,3-dimethylpiperidinium bis(trifluoromethylsulfonyl)imide; 1-butyl-1,3-dimethylpiperidinium dicyanamide; 1-butyl-3-methylimidazolium bis(trifluoromethylsulfonyl)imide; 1-hexyl-3-methylimidazolium chloride; 1-ethyl-3-methylimidazolium bis(trifluoromethylsulfonyl)imide; 1-butyl-3-methylimidazolium tetrafluoroborate; 1-ethyl-3-methylimidazolium acetate; 1-ethyl-3-methylimidazolium thiocyanate; 1-ethyl-3-methylimidazolium ethylsulfate; N,N-dimethylethanolamine acetate and combinations thereof, but is not limited thereto. Any known ionic solvent can be used, with preferred ionic solvents being those that have a boiling point of about 200° C. or greater, which is the temperature at which reaction yield increases. As such, reaction yield can be increased while ionic solvent is removed and recovered.

In addition, in the case where the synthetic reaction is carried by adding lactic acid oligomers to an ionic solvent, it is possible to reduce the amount of the ionic solvent. Generally, the present invention adds the ionic solvent in a low amount of about 20 parts by weight based on 100 parts by weight of the lactic acid oligomers, while still making it possible to synthesize lactide at a high yield. While the present method allows for the addition of such small amounts of ionic solvent, there is no limitation to the amount of ionic solvent added. Thus, for example, it is possible to synthesize lactide by reacting lactic acid oligomers in the presence of an excessive amount of ionic solvent.

In an exemplary embodiment of the present invention, when the lactic acid oligomers are used in the step (a), lactide can be synthesized by using the lactic acid oligomers having a molecular weight of about 600 to 9000 g/mol.

In an exemplary embodiment of the present invention, a catalyst is further added to the step of lactide synthesis. Any suitable catalysts can be used in the method of the present invention and preferably, the catalyst is selected from the group consisting of $Al(iso-PrO)_3$; $Al(ethyl\ acetoacetate)_3$; $Al(AlO(iso-PrO))_3$; $Ti(iso-PrO)_4$; $Ti((iso-PrO)_2(acethylacetonate))_2$; $Ti(acethylacetonate)_4$; $Zn(hexanoate)_2$; $Zn(stearate)_2$; $Zn(naphthenate)_2$; $ZnCl_2$; $ZnO$; $Zr(n-PrO)_4$; $ZrO(stearate)_2$; $Zr(acethylacetonate)_4$; $Zr(n-BuO)_3(acethylacetonate)$; $ZrO(AcO)_2$; $ZrO(OH)_2$; $ZrO_2$; $Sn(octoate)_2$; and combinations thereof. In general, any catalysts that include a metal such as Ti, Zn, Zr, Sn or Al and are capable of increasing a reaction yield can be used.

In an exemplary embodiment of the present invention, it is possible to continuously synthesize lactide by sequentially adding the lactic acid oligomers after the synthesis of lactide is completed.

Further, according to the present method, the ionic liquid does not participate in the synthetic reaction, and thus, it can be used sequentially in the following continuous reactions. Because the ionic liquid exists in a liquid state at room temperature, simple washing of a reactor can be optionally carried out by using the ionic liquid as a medium. The term "simple washing" as used herein refers to simple rinse-out rather than a complicated washing of the whole reactor that is typically required of a reactor in which lactide is prepared. Therefore, the present invention provides an eco-friendly method for preparing lactide which is characterized by minimizing unnecessary processing, such as reactor washing, and which reduces the amount of a solvent used in the reaction.

EXAMPLES

The following examples illustrate the invention and are not intended to limit the same.

Example: 1

Lactic acid oligomers were prepared by using lactic acid monomer at 150° C., 0.3 atm (228 mmHg) for 2 hours, and then, based on 100 parts by weight of the lactic acid oligomers that would be converted into lactide, 50 parts by weight of 1-butyl-3-methylimidazolium chloride as an ionic liquid were added thereto. After that, 0.05 parts by weight of ZnO as a catalyst was added to the resulting mixture based on 100 parts by weight of the lactic acid oligomers, followed by performing the synthetic reaction of lactide at 150° C., 0.05 atm (38 mmHg) for 2 hours.

After the synthetic reaction was completed, lactide was obtained with a yield of 80% or greater, and the reaction was progressed continuously.

Example: 2

Lactic acid oligomers were prepared by using lactic acid monomers at 150° C., 0.3 atm (228 mmHg) for 2 hours, followed by introducing the lactic acid oligomers into a reactor where lactide was synthesized by using 1-butyl-3-methylimidazolium chloride. Under the same conditions of lactide synthesis as described in Example 1, lactide was continuously synthesized for 2 hours.

After the synthetic reaction was completed, lactide was obtained as the amount of the lactic acid oligomers added thereto (i.e., lactide was produced in about the same amount as the lactic acid oligomers used). In particular, the lactide was produced with a yield of greater than about 80% of the amount of oligomer added after the production of the first lactide.

Example: 3

Lactide was synthesized according to the same conditions as described in Example 1 except that $LiCO_3$ was used as a catalyst. After the synthetic reaction was carried out 2 hours, lactide was synthesized with a yield of 85% or greater (wherein the yield is the amount of lactide synthesized based on the amount of lactic acid oligomers used).

Example: 4

Lactide was synthesized according to the same conditions as described in Example 1 except that 1-butyl-3-methylimidazolium chloride as an ionic liquid was used in an amount of 30 pats by weight based on 100 parts by weight of the lactic acid oligomers. After the synthetic reaction was carried out 2 hours, lactide was synthesized with a yield of 80% (based on the amount of lactic acid oligomers added).

Comparative Example: 1

Lactic acid oligomers were prepared by using lactic acid monomers at 150° C., 0.3 atm (228 mmHg) for 2 hours, and ZnO as a catalyst was added thereto in an amount of 0.05 wt % based on the amount of lactic acid oligomers. The resulting mixture was subjected to a lactide synthetic reaction at 150° C., 0.05 atm.

The synthetic reaction was carried out 1 hour, but there was little synthetic reaction. The yield (lactide) of the synthesis was about 15% (based on the amount of lactic acid oligomer added), and the majority reaction product was lactic acid (i.e. a majority of the remaining 85% produced by the reaction). In particular, 15% of lactide was produced from the initial input of oligomers and most of the remainder is present in the oligomer state.

Comparative Example: 2

After the reaction according to Comparative Example 1 was completed, the resulting mixture was subjected to a further reaction at 160° C. for 3 hours. As a result, about a 15% yield of lactide was synthesized (based on the amount of lactic acid oligomer added). However, no additional synthetic reaction occurred.

Comparative Example: 3

Lactic acid oligomers were prepared by using lactic acid monomer at 150° C., 0.3 atm (228 mmHg) for 2 hours, and ZnO as a catalyst was added thereto in an amount of 0.05 wt % based on the amount of lactic acid oligomer. The resulting mixture was subjected to a lactide synthetic reaction at 205° C. and 0.05 atm or lower. After the synthetic reaction was carried out 2 hours, lactide was synthesized with a yield of 80% (based on the amount of lactic acid oligomers added).

As demonstrated, the preparation method of the present invention was capable of consecutively synthesizing lactide with a yield of about 85% or greater (based on the amount of lactic acid oligomers added) at a reaction temperature of about 150° C. On the other hand, the preparation method according to Comparative Examples was capable of merely synthesizing lactide with a yield of about 15% at a reaction temperature of about 160° C. in a non-consecutive manner, and could only non-consecutively synthesize lactide with a yield of 85% of greater at a reaction temperature of about 205° C.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A method for preparing lactide, comprising:
    (a) synthesizing one or more lactic acid oligomers by polymerization of at least one lactic acid monomer;
    (b) adding an ionic solvent to the synthesized one or more lactic acid oligomers; and
    (c) synthesizing lactide from the one or more lactic acid oligomers added to the ionic solvent,
    wherein the synthesis of lactides in the step (c) is carried out at a temperature of about 100 to 1000° C. under a pressure of about 1 to 600 mmHg for about 1 to 5 hours, and the ionic solvent is selected from the group consisting of 1-butyl-1-methyl-azepanum bis(trifluoromethylsulfonyl)imide; 1-butyl-1-methyl-azepanum dicyanamide; 6-azonia-spiro[5,6]dodecan bis(trifluoromethylsulfonyl)imide; 6-azonia-spiro[5,6]dodecan dicyanamide; 1-benzyl-3-methylimidazolium chloride 1-butyl-1,3-dimethylpiperidinium bis(trifluoromethylsulfonyl)imide; 1-butyl-1,3-dimethylpiperidinium dicyanamide; 1-butyl-3-methylimidazolium bis(trifluoromethylsulfonyl)imide; 1-hexyl-3-methylimidazolium chloride; 1-ethyl-3-methylimidazolium bis(trifluoromethylsulfonyl)imide; 1-butyl-3-methylimidazolium tetrafluoroborate; 1-ethyl-3-methylimidazolium acetate; 1-ethyl-3-methylimidazolium thiocyanate; 1-ethyl-3-methylimidazolium ethylsulfate, N,N-dimethylethanolamine acetate and combinations thereof.

2. The method of claim 1, wherein the polymerization of the lactic acid monomer in the step (a) is carried out at a temperature of about 120 to 300° C. under a pressure of about 1 to 500 mmHg for about 1 to 5 hours.

3. The method of claim 1, wherein the one or more lactic acid oligomers have a molecular weight of about 600 to 9000 g/mol.

4. The method of claim 1, wherein the synthesis of lactide from the one or more lactic acid oligomers in the step (c) is carried out in the presence of a catalyst.

5. The method of claim 4, wherein the catalyst is selected from the group consisting of Al(iso-PrO); Al(ethyl acetoacetate); Al(AlO(iso-PrO)); Ti(iso-PrO); Ti((iso-PrO)$_2$(acetylacetonate)); Ti(acethylacetonate); Zn(hexanoate); Zn(stearate); Zn(naphthenate); ZnCl; ZnO; Zr(n-PrO); ZrO(stearate); Zr(acetylacetonate); Zr(n-BuO)(acetylacetonate); ZrO(AcO); ZrO(OH); LiCO; ZrO; Sn(octoate); and combinations thereof.

6. The method of claim 1, which further comprises the steps of adding one or more lactic acid oligomers and synthesizing lactide therefrom continuously after lactide is synthesized in the step (c).

* * * * *